United States Patent
Padmanabhan et al.

(10) Patent No.: US 11,944,632 B2
(45) Date of Patent: Apr. 2, 2024

(54) USE OF SODIUM DICHLOROISOCYANURATE (NADCC) AND A PHARMACEUTICAL FORMULATION PREPARED THEREFROM

(71) Applicant: SAVA HEALTHCARE LTD, Maharashtra (IN)

(72) Inventors: Sriram Padmanabhan, Bangalore (IN); Vinod Ramchandra Jadhav, Dubai (AE)

(73) Assignee: SAVA HEALTHCARE LTD, Maharashtra (IN)

( * ) Notice: Subject to any disclaimer, the term of this patent is extended or adjusted under 35 U.S.C. 154(b) by 0 days.

(21) Appl. No.: 17/520,787

(22) Filed: Nov. 8, 2021

(65) Prior Publication Data
US 2023/0076066 A1  Mar. 9, 2023

Related U.S. Application Data (60) Provisional application No. 63/110,516, filed on Nov. 6, 2020.

(51) Int. Cl.
| | |
|---|---|
| A61K 31/53 | (2006.01) |
| A61K 9/00 | (2006.01) |
| A61K 9/16 | (2006.01) |
| A61K 31/4045 | (2006.01) |
| A61K 31/4706 | (2006.01) |
| A61K 31/4965 | (2006.01) |
| A61K 31/675 | (2006.01) |
| A61K 31/7048 | (2006.01) |
| A61K 31/7056 | (2006.01) |
| A61K 38/13 | (2006.01) |
| A61K 38/21 | (2006.01) |
| A61K 39/395 | (2006.01) |
| A61P 31/14 | (2006.01) |

(52) U.S. Cl.
CPC ............ *A61K 31/53* (2013.01); *A61K 9/0075* (2013.01); *A61K 9/1623* (2013.01); *A61K 31/4045* (2013.01); *A61K 31/4706* (2013.01); *A61K 31/4965* (2013.01); *A61K 31/675* (2013.01); *A61K 31/7048* (2013.01); *A61K 31/7056* (2013.01); *A61K 38/13* (2013.01); *A61K 38/21* (2013.01); *A61K 39/3955* (2013.01); *A61P 31/14* (2018.01)

(58) Field of Classification Search
CPC ...... A61K 31/53; A61K 9/0075; A61K 9/1623
See application file for complete search history.

(56) References Cited

U.S. PATENT DOCUMENTS

2006/0276339 A1 * 12/2006 Windsor ................ A01N 41/06
514/369

* cited by examiner

*Primary Examiner* — Michael B. Pallay
(74) *Attorney, Agent, or Firm* — Schneider IP Law; Jerold I. Schneider (57) ABSTRACT

The present disclosure relates to use of Sodium 3,5-dichloro-2,4,6-trioxo-1,3,5-triazinan-1-ide having a chemical structure:

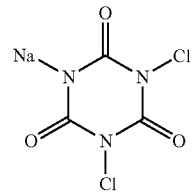

for the treatment and/or prevention of COVID-19 infection. The present disclosure further relates to a pharmaceutical formulation that is administered in the form of dry powder inhalation (DPI) to the subject. The dry powder inhalation formulation comprises a micronized Sodium 3,5-dichloro-2,4,6-trioxo-1,3,5-triazinan-1-ide, a first lactose, a second lactose, and at least one excipient. The pharmaceutical formulation of the present disclosure increases the bioavailability of the NaDCC, has patient compliance, and reduced adverse effects.

17 Claims, 4 Drawing Sheets
(4 of 4 Drawing Sheet(s) Filed in Color)

USE OF SODIUM DICHLOROISOCYANURATE (NADCC) AND A PHARMACEUTICAL FORMULATION PREPARED THEREFROM

FIELD

The present disclosure relates to a novel use of Sodium dichloroisocyanurate (NaDCC) and a pharmaceutical formulation prepared therefrom. Particularly, the present disclosure relates to a novel use of Sodium dichloroisocyanurate (NaDCC) for inhibition of COVID-19 infection caused by COVID-2 virus.

Definitions

As used in the present disclosure, the following terms are generally intended to have the meaning as set forth below, except to the extent that the context in which they are used indicates otherwise.
- D10 refers to the portion of particles with diameters below the specified value is 10%.
- D50 refers to the portion of particles with diameters smaller and larger than a specified value are 50%. Also known as the median diameter.
- D90 refers to the portion of particles with diameters below the specified value is 90%.
- MMAD (mass median aerodynamic diameter) refers to the diameter at which 50% of the particles of an aerosol by mass are larger and 50% are smaller.
- Coronavirus disease 2019 (COVID-19) is defined as illness caused by a novel coronavirus now called as severe acute respiratory syndrome coronavirus 2 (SARS-CoV-2; formerly called 2019-nCoV).

BACKGROUND

The background information herein below relates to the present disclosure but is not necessarily prior art.

Currently, amongst numerous disinfectant (like Povidone iodine, Benzalkonium Chloride; Alkyl Dimethyl Ethylbenzyl Ammonium Chloride, Potassium Peroxymonosulfate, Phenol; Phenolate Sodium, Hydrogen Peroxide, ethanol, isopropyl alcohol etc.) against COVID-2, hypochlorous acid (HOCl) is usually recommended. The mechanism of disinfection involves the destroying of the cell wall of microbes or viruses, allowing the disinfectant to destroy or inactivate them. Hypochlorous acid (HOCl) is the most effective chemical against pathogens, wherein HOCl targets bacteria or virus by chemically linking chlorine atoms to nucleotide bases that disrupt the function of bacterial DNA, impede metabolic pathways in which cells use enzymes to oxidize nutrients and release energy and other membrane-associated activities.

Further, Hypochlorous acid (an oxidant) is very well known in the art which is widely used as a source of chlorine and exerts biocidal effect by attacking the surface and plasma membrane proteins of bacterial cells impairing transport of solutes and the salt balance. Still further, Hypochlorous acid is a natural biocide, produced by the human body's natural immune system via Oxidative Burst Pathway to destroy the invading microorganisms during infection. Neutrophils release, a burst of bactericidal chemicals, including HOCl (powerful oxidizing agent) upon contact with the pathogen, kills the pathogen by tearing down the cell membranes and proteins. However, it is believed that HOCl does not enter freely into eukaryotic cell that restricts the selectivity of hypochlorous solutions. Only 20 micro mole-HOCl was required for 50% inhibition of bacterial growth ($5\times10^8$) *Escherichia coli*/ml), and 50 microM HOCl completely inhibited cell division. The biocidal effects of HOCl solutions did not depend on the available chlorine concentration, but on the HOCl concentration.

Stability of the HOCl solution is pH dependent, so the pH of the HOCl solution must be maintained within the range of 3 to 6 to prevent its dissociation and biocidal activity. At pH >6, the dissociation leads to generation of hypochlorite (OCl—) while below pH 3, it produces a higher concentration of chlorine ($Cl_2$). In another research it was found that HOCl loses its stability when exposed to ultraviolet light, sunshine, air, and higher temperatures (≥77° F.). The stability limitation affects the shelf life of HOCl products which last for a month once the bottle is opened. To attain the stability, the products need to be stored in a glass opaque bottle. Therefore, it is important to read the manufacturer's instructions on whether an open bottle affects the expiration date.

Further, due to non-availability of any specific treatment for COVID-19, clinicians are relying on their knowledge in treating SARS, MERS, and other previous influenza viruses for the population affected by COVID-19. Clinical trials for vaccine or a treatment drug are still underway and some of the drugs being tested in clinical phase trials includes Favipiravir, ribavirin, Lopinavir, ritonavir, Remdesivir, Arbidol, Ivermectin, Chloroquine, hydroxychloroquine, Cyclosporin A, interferons, Tocilizumab, and plasma therapy; each of them having its own limitations and efficacy success. These factors go to reiterate a lack of approved therapy strategy and options for the COVID-19 infection.

Therefore, there is felt a need to provide a compound that is effective in the prevention and treatment of Covid-19 (Coronavirus).

Objects

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide Sodium dichioroisocyanurate (NaDCC) for the prevention and treatment of COVID-19 and other viruses.

Another object of the present disclosure is to provide a pharmaceutical formulation comprising NaDCC.

Another object of the present disclosure is to provide a pharmaceutical formulation comprising NaDCC that is used in the prevention and treatment of COVID-19 and other viruses such as enveloped viruses, EBOLA virus, HIV, HBV, HCV, influenza virus, MERS, and SARS.

Still another object of the present disclosure is to provide Sodium dichloroisocyanurate (NaDCC) as a disinfectant, wound healing agent, an antibacterial agent, and an antifungal agent.

Yet another object of the present disclosure is to provide a process for the preparation of a pharmaceutical formulation comprising Sodium dichloroisocyanurate (NaDCC).

Another object of the present disclosure is to provide a NaDCC formulation in the form of dry powder inhalation that is effective.

Still another object of the present disclosure is to provide a NaDCC formulation in presence of lowest concentration of hydrogen peroxide to yield stabilized chlorine dioxide which could help as a wound healing agent, cleaning agent and a topical hand sanitizers.

Yet another object of the present disclosure is to provide a formulation comprising NaDCC that is safe, stable, efficient, economic, and convenient to use.

Other objects and advantages of the present disclosure will be more apparent from the following description, which is not intended to limit the scope of the present disclosure.

SUMMARY

The present disclosure relates to use of Sodium 3,5-dichloro-2,4,6-trioxo-1,3,5-triazinan-1-ide having a chemical structure:

for the treatment and/or prevention of COVID-19 infection.

Further, the present disclosure relates to a pharmaceutical formulation.

In an aspect, the pharmaceutical formulation comprises a micronized Sodium 3,5-dichloro-2,4,6-trioxo-1,3,5-triazinan-1-ide (NaDCC) having a particle size in the range of 3 μm to 7 μm, a first lactose having a particle size in the range of 15 μm to 120 μm, a second lactose having a particle size in the range of 1 μm to 70 μm, and at least one excipient. The weight ratio of the first lactose to the second lactose is in the range of 4:1 to 10:1. The first lactose and the second lactose are adsorbed on the surface of the micronized Sodium 3,5-dichloro-2,4,6-trioxo-1,3,5-triazinan-1-ide (NaDCC). The pharmaceutical formulation is in the form of inhalable dry powder.

BRIEF DESCRIPTION OF THE ACCOMPANYING DRAWING

The patent or application file contains at least one drawing executed in color. Copies of this patent or patent application publication with color drawing(s) will be provided by the Office upon request and payment of the necessary fee.

The present disclosure will now be described with the help of the accompanying drawing, in which.

DETAILED DESCRIPTION

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

Coronaviruses are a large family of viruses that cause illness in humans and animals.

The present disclosure relates to use of Sodium 3,5-dichloro-2,4,6-trioxo-1,3,5-triazinan-1-ide having a chemical structure:

for a treatment and/or prevention of COVID-19 infection.

NaDCC has been shown to be an effective antimicrobial agent and anti-COVID agent. The capacity of NaDCC to continue to release significant amounts of HOCl allows it to operate over a wider pH range.

NaDCC produces hypochlorous acid, a well-known oxidizing agent.

$$NaOCl + H_2O \rightarrow HOCl + NaOH$$

Sodium Hypochlorite Dispersion in Water $$NaCl_2(NCOI)_3 + 2H_2O \rightarrow 22HOCl + NaH_2(NCOI)_3$$

NaDCC Dissolution in Water

NaDCC has a shelf life of 5 years in temperate and tropical climates. The antimicrobial activity of NaDCC is independent of pH and temperature, and is found to be effective on 29 Gram-positive and 29 Gram-negative bacteria, as well as 66 fungi. The use of NaDCC has been recommended for washing of vegetables, fruits and other edible items and above all in disinfecting feeding Bottles and teats. NaDCC at a concentration of 25 mg/ml removed all coliforms and E. coli from low turbidity water by 1.8-2.8 logs of viable bacteria from raw river water. Bacterial membrane disruption and release of cell contents is not observed at concentrations below 5 mM HOCl.

In an embodiment, the present disclosure further relates to pharmaceutical a formulation comprises:
- a micronized Sodium 3,5-dichloro-2,4,6-trioxo-1,3,5-triazinan-1-ide having a particle size in the range of 3 μm to 7 μm;
- a first lactose having a particle size in the range of 15 μm to 120 μm;
- a second lactose having a particle size in the range of 1 μm to 70 μm; and
- at least one excipient.

In an embodiment, the micronized Sodium 3,5-dichloro-2,4,6-trioxo-1,3,5-triazinan-1-ide (NaDCC) is in an amount in the range of 25 wt % to 65 wt % with respect to the total weight of the formulation.

In an embodiment, the first lactose is in an amount in the range of 25 wt % to 65 wt % with respect to the total weight of the formulation.

In an embodiment, the mean particle size (d10) of the first lactose is in the range of 19 μm to 43 μm.

In an embodiment, the mean particle size (d50) of the first lactose is in the range of 53 μm to 66 μm.

In an embodiment, the mean particle size (d90) of the first lactose is in the range of 75 μm to 106 μm.

In an embodiment, the first lactose is respitose SV003.

In an embodiment, the second lactose is in an amount in the range of 2 wt % to 15 wt % with respect to the total weight of the formulation.

In an embodiment, the mean particle size (d10) of the second lactose is in the range of 1 μm to 4 μm.

In an embodiment, the mean particle size (d50) of the second lactose is in the range of 10 μm to 25 μm.

In an embodiment, the mean particle size (d90) of the second lactose is in the range of 30 μm to 65 μm.

In an embodiment, the second lactose is respitose ML006.

In an embodiment, a weight ratio of the first lactose to the second lactose is in the range of 4:1 to 10:1.

In an embodiment, at least one excipient is in an amount in the range of 20 wt % to 80 wt % with respect to the total weight of the formulation.

In an embodiment, the excipient is selected from glacial acetic acid, cyanuric acid, citric acid, magnesium stearate, hydrophilic colloidal silica such as AEROSIL 200, L-Leucine.

In an embodiment of the present disclosure, citric acid, magnesium stearate, hydrophilic colloidal silica such as AEROSIL 200 and L-Leucine acts as dispersibility enhancers which is added to NaDCC DPI that targets higher concentration of NaDCC in the fine particle fraction (FPF) of NaDCC DPI. The dispersibility enhancer will also prevent coagulation disorders that is commonly found in COVID-19 patients.

In an embodiment, the first lactose and the second lactose are adsorbed on the surface of the micronized Sodium 3,5-dichloro-2,4,6-trioxo-1,3,5-triazinan-1-ide (NaDCC).

The lactose used in the present disclosure is well-known which is used as a carrier to distribute the actives during inhalation.

In an embodiment, the pharmaceutical formulation is administered to the subject via inhalation route in the form of dry powder inhalation.

In an exemplary embodiment, the pharmaceutical formulation is administered to the subject via inhalation route in the form of dry powder inhalation using pressurized metered-dose inhalation, unit-dose device, multiple unit-dose device, and reservoir device.

In an embodiment, the median mass aerodynamic diameter (MMAD) of the pharmaceutical formulation in the form of dry powder inhalation is in the range of 2 μm to 5 μm.

In an embodiment, the lung to plasma ratio of Sodium 3,5-dichloro-2,4,6-trioxo-1,3,5-triazinan-1-ide is in the range of 25 to 50 wt %.

In an embodiment, the formulation has an antibacterial activity, wound healing activity and antifungal activity.

The pharmaceutical formulation is used in the treatment and/or prevention of SARS COVID-19 infection and other viruses such as enveloped viruses, EBOLA virus, HIV, HBV, HCV, influenza virus, and MERS.

In an embodiment, the pharmaceutical formulation further comprise at least one anti-viral drug.

In an embodiment, the anti-viral drug is selected from the dexamethasone, Ivermectin, Favipiravir, Ribavirin, Lopinavir, Ritonavir, Remdesivir, Arbidol, Chloroquine, Hydroxychloroquine, Cyclosporin A, Interferons, and Tocilizumab.

In an embodiment, the pharmaceutical formulation is in a dosage form selected from dry powder, solution, nasal spray, and hydrogel.

In an embodiment, the pharmaceutical formulation of the present disclosure, is stabilized in various forms and can be stored at room temperature (ambient to 37° C.).

In another embodiment, the present disclosure still further discloses sodium dichioroisocyanurate for disinfecting damaged or affected mammalian tissue, including wounds and burns; disinfecting or cleansing surfaces; and treating food products and herbal extracts along with preservation of consumable products for human consumption.

In an embodiment, the wound healing solution comprises a predetermined amount of NaDCC, lime splash as a fragrance, and water.

In another embodiment, the wound healing hydrogel comprises a predetermined amount of NaDCC, Carbopol, water, and lime splash.

In another aspect of the present disclosure, there is provided a process for the preparation of the pharmaceutical formulation in the form of dry powder inhalation.

The process is described in detail.

In a first step, a first lactose and a second lactose are blended to obtain the lactose mixture. The lactose mixture is sifted through 80 mesh in a controlled temperature and humidity conditions to obtain a homogeneous lactose mixture.

In a second step, excipient is sifted through 80 mesh and mixed with the homogenous lactose mixture to obtain a resultant mixture.

In a third step, separately, NaDCC is sifted through 80 mesh and blended with the resultant mixture at 15 RPM for 20 mins to obtain a pharmaceutical formulation in the form of dry powder inhalation (DPI).

The so obtained pharmaceutical formulation is loaded into size 3 HPMC (Hydroxypropyl methylcellulose) capsules using a capsule filler.

In another embodiment of the present disclosure, there is provided a stable NaDCC formulation with the use of micronized excipients such as mannitol, trehalose, sorbitol, dextrose at ratios of 20 to 80% in place of lactose. Since mannitol rehydrates mucus and changes the properties of bronchi walls, that acts to enhance airway clearance by improving interaction between cilia and mucus. It is beneficial for treatment of viral diseases affecting the lungs. Trehalose, a nonreducing sugar, can efficiently improve dry powder aerosolization by increasing the FPF and has distinguished similarities to the pulmonary sugar carrier, lactose monohydrate, as both are crystalline disaccharides and both are hydrates.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be tested to scale up to industrial/commercial scale and the results obtained can be extrapolated to industrial scale.

EXPERIMENTAL DETAILS

Example 1: Preparation of Dry Powder Inhalation of Sodium Dichloroisocyanurate in Accordance with the Present Disclosure 7.5 g of micronized NaDCC, 4.5 g Respitose SV003 IP, and 0.5 g Respitose ML006 USP NF were weighed. All the materials were passed through the sieve no. 80 and mixed properly to obtain a dry powder formulation comprising NaDCC, respitose SV003 IP and respitose ML6 USP. The dry powder formulation comprising NaDCC, respitose SV003 IP and respitose ML006 USP were filled in HPMC (hydroxylpropyl methylcellulose) based, non-stick, and reddish brown/transparent capsule having size of 3.

TABLE 1

NaDCC Dry powder for inhalation

| Mixing | mg/Capsule | % Formulation | qty in gm. | After Calculation (gm.) |
|---|---|---|---|---|
| Micronized (NaDCC) | 15 | 60 | 7.5 | 7.5 |
| Respitose SV003 IP (first lactose) | 9 | 36 | 4.5 | 4.5 |
| Respitose ML006 USP NF (Second lactose) | 1 | 4 | 0.5 | 0.5 |
| Total weight of the powder | 25 | 100 | 12.5 | 12.5 |
| HPMC, non-stick, Reddish Brown/Transparent capsule, Size 3 | 1 No. | | 500 No. | 500 No. |

Example 2

The dry powder inhalation formulations were prepared in the similar manner as described in Example 1, by varying the concentration of ingredients/components as tabulated in Table 2:

TABLE 2

NaDCC Dry powder for inhalation

| Mixing | mg/Capsule | % Formulation | qty in gm. | After Calculation (gm.) |
|---|---|---|---|---|
| Micronized (NaDCC) | 7 | 28 | 3.5 | 3.5 |
| Respitose SV003 IP (first lactose) | 15.5 | 62 | 7.75 | 7.75 |
| Respitose ML006 USP NF (second lactose) | 2.5 | 10 | 1.25 | 1.25 |
| Total weight of the powder | 25 | 100 | 12.5 | 12.5 |
| HPMC, non-stick, Reddish Brown/Transparent capsule, Size 3 | 1 No. | | 500 No. | 500 No. |

TABLE 3

NaDCC DPI 7 mg

| Sr. No. | Ingredient | Mg/Capsule | Analysis |
|---|---|---|---|
| 1 | 3NC (Micronized NaDCC) | 7.00 | Assay: 98.12% |
| 2 | Syloid FP244 IH (colloidal silica) | 1.3750 | |
| 3 | Respitose SV003 USP NF (first lactose) | 14.125 | |
| 4 | Respitose ML006 USPNF (second lactose) | 2.500 | |
| | Total weight | 25 | |
| 5 | HPMC, Size "3", Non-stick, Red trans/Trans cap | 1.0 No. | |

Example 3: NaDCC DPI—Stability Study

The stability conditions of NaDCC DPI are illustrated below in Table 4.

TABLE 4

Stability Result

Product Name: NaDCC DPI 7 mg
Batch Size: 1000 capsules

| | | | Tests | | | |
|---|---|---|---|---|---|---|
| | | Description | Assay | T0 | T1 | T2 |
| Pack 1: HDPE bottle | Limit | *** | 90-110% | | | |
| | Initial Composite Assay | *** | 106.2% | | Not Done | |
| | 1M/2-8 | *** | 100.5% | | | |
| | 1M/25/60% | *** | 97.3% | | | |
| | 1M/30/75% | *** | 95.4% | | | |
| | 1M/40/75% | *** | 49.8% | | | |
| | 3M/2-8 | *** | 102.3% | 10.6% | 60.9% | 29.420% |
| | 3M/25/60% | *** | 96.0% | 10.6% | 56.4% | 20.840% |
| | 3M/30/75% | *** | 81.9% | 9.0% | 51.1% | 16.750% |
| | 3M/40/75% | *** | 3.1% | | Not done | |

*** White to off white powder

Inference: The dry powder inhalation (DPI) formulation of NaDCC in capsules of the present disclosure was subjected to 1 and 3 months stability testing at 25° C./60% RH and 40° C./75% RH respectively. It is evident from table 4 that NaDCC (API) is stable for a longer period of time, at 25° C./60% RH, and 40° C./75% RH conditions as there was no change in the NaDCC content in dry powder inhalation (DPI) formulations of NaDCC 7 mg.

The so obtained dry powder inhalation formulation was filled into a size 3 HPMC capsule using a capsule filler.

Further, the so obtained NaDCC DPI was clinically assessed by determining the amount of cyanuric acid in the tissues.

Cyanuric acid was not detected in the lung homogenate samples of control animals and test animals' samples. However, in the test sample, cyanuric acid was seen at 0.004% by HPLC. This reflects that NaDCC was metabolized fast with a short half-life and not accumulated in tissues in the amount administered as a DPI. Free available chlorine by titrimetry method also not detected in any sample tested from the study confirming the results of cyanuric acid estimation. The inhaled NaDCC appears to be extensively metabolized and therefore be well tolerated in the chronic treatment of asthma and other chronic lung infections.

Example 4: % Microbial Load Reduction in Ayurvedic Herbs and Extracts by Using Sodium Dichloroisocyanurate (NaDCC)

TABLE 5

| S.N. | Batch | Parameter | Total cfu/g | % microbial reduction |
|---|---|---|---|---|
| 1 | RDP/SR/011903 | Untreated | 21000 | Not applicable |
| 2 | RDP/SR/073 | 10 g of Salacia extract is mixed with 0.02 g of NaDCC (0.2.% of input extract) and triturate well in mortar and pestle to get fine powdered extract. | <10 | >99% reduction |

TABLE 5-continued

| S.N. | Batch | Parameter | Total cfu/g | % microbial reduction |
|---|---|---|---|---|
| 3 | RDP/SR/074 | 10 g of Salacia extract is mixed with 0.04 g of NaDCC (0.4% of input extract) and triturate well in mortar and pestle to get fine powdered extract. | <10 | >99% reduction |

Inference: From the table 5 it is evident that, sodium dichloroisocyanurate (NaDCC) in an amount in the range of 0.05% to 5% when mixed with Salacia extract shows antibacterial activity and can reduce the bacterial load by 99.99% (which is 4 logs reduction in bacterial counts).

Example 5: Antibacterial and an Antifungal Activity of Sodium Dichloroisocyanurate (NaDCC) in Accordance with the Present Disclosure The bacteria (Bacillus licheniformis, and Bacillus paralicheniformis) and fungus (Aspergillus sps) isolated from the Salacia reticulata and bacteria Bacillus licheniformis isolated from Garcinia cambogia extract was tested for susceptibility for the sensitivity towards NaDCC.

Figure 1:
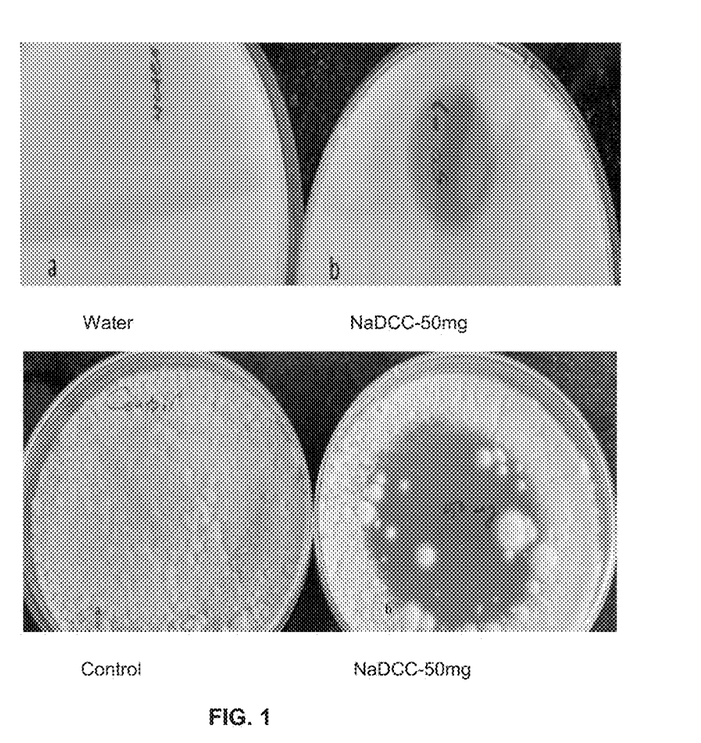
FIG. 1 illustrates an effective antibacterial activity and anti-fungal activity of NaDCC towards bacteria and fungus isolated from *Salacia reticulata* root extract.
Figure 2:
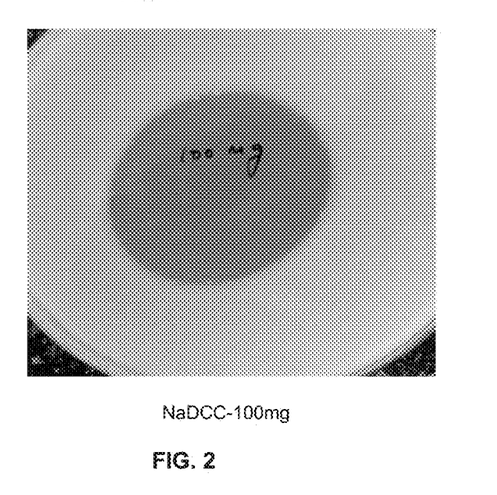
FIG. 2 illustrates an effective antibacterial activity of NaDCC towards bacteria isolated from *Garcinia cambogia* fruit rind extract.

FIG. 1 illustrated an effective antibacterial activity and anti-fungal activity of NaDCC towards bacteria and fungus isolated from Salacia reticulata; and FIG. 2 shows illustrated an effective antibacterial activity of NaDCC towards bacteria isolated from Garcinia cambogia extract.

Figure 3A:
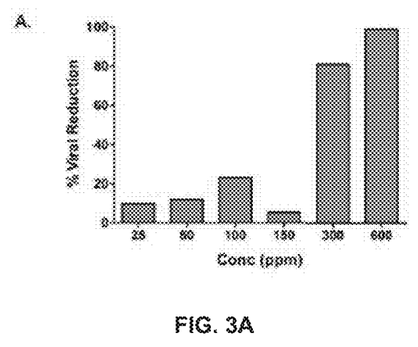
FIG. 3A and FIG. 3B illustrate the % inhibition of COVID-19 virus with respect to the reduction of replication of virus and enhancement of mammalian cell vero6 survival (cytotoxicity) respectively.
Figure 3B:
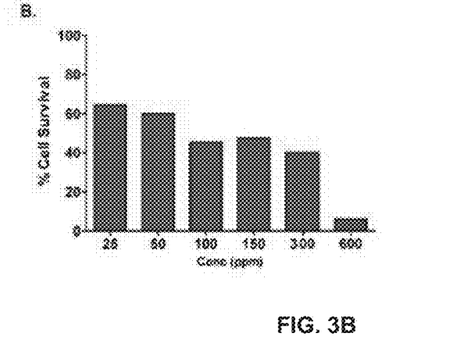

Example 6: Anti-COVID Activity of Sodium Dichloroisocyanurate (NaDCC) as Per the Present Disclosure FIG. 3A and FIG. 3B clearly indicated that NaDCC effectively reduce the replication of virus and increase the survival of cell. At 600 ppm concentration, NaDCC shows greater than 99.99% inhibition of the virus replication.

Example 7: Wound Healing Activity of Sodium Dichloroisocyanurate (NaDCC) in Dogs and Cats in Accordance with the Present Disclosure

TABLE 6

Batch using acetic acid for stability studies

NaDCC Solution

| Ingredient | mg/ml | % | ml |
|---|---|---|---|
| Batch size | | | 200 |
| 3NC (NaDCC) | 1.670 | 0.167 | 0.348 |
| Acetic acid | 998.33 | 99.833 | qs |
| Total | 1 | 100 | 200 |

TABLE 7

Stability of the NaDCC in the solution:

Product Name: NaDCC Solution
Batch Size: 200 ml

| | Limit | Description *** | Available Chlorine mg/ml | pH |
|---|---|---|---|---|
| HDPE bottle | Initial | *** | 0.954 | 1.28 |
| HDPE bottle | 1 Month 2-8 | *** | 0.801 | 0.51 |
| | 1 Month 25/60 | *** | 0.922 | 0.52 |
| | 1 Month 40/75 | *** | 0.563 | 0.57 |

*** Clear colourless solution filled in 30 cc HDPE bottle

TABLE 8

Batch using acetic acid + cyanuric acid for stability studies

| Ingredient | mg/ml | % | ml |
|---|---|---|---|
| Batch size | | | 200 |
| NaDCC | 1.670 | 0.167 | 0.348 |
| Cyanuric acid | 0.100 | 0.01 | 0.020 |
| Acetic acid | qs to 1 ml | qs | qs |
| Total | 1 | 100 | 200 |

TABLE 9

Stability data report:

Product Name: NaDCC Solution
Batch Size: 200 ml

| | Limit | Description *** | Available Chlorine mg/ml | pH |
|---|---|---|---|---|
| HDPE bottle | Initial | *** | 1.003 | 1.30 |
| HDPE bottle | 1 Month 2-8 | *** | 0.702 | 0.7 |
| | 1 Month 25/60 | *** | 0.921 | 0.75 |
| | 1 Month 40/75 | *** | 0.521 | 0.72 |

*** Clear colourless solution filled in 30 cc HDPE bottle

Inference:

From the tables 6 to 9 it is evident that, the Sodium dichloroisocyaniurate (NaDCC) is stable in acetic acid and cyanuric acid as a solution and can be used as a wound healing agent in cats and dogs with an appropriate dilutions of the solution (1% to 5% working solution to be made by freshly diluting with water). The stability studies indicate the level of residual free chlorine, which is the active ingredient for wound healing.

Further, it is also noted that commercially known product such as Microdacyn has wound healing activity due to the presence of hypochlorous acid (one molecule of HOCl) in the formulation. Therefore, NaDCC formulation has enhanced wound healing activity as upon hydrolysis NaDCC formulation results in the formation of two molecules of HOCl (which has wound healing activity).

Example 8: Efficacy of Sodium Dichloroisocyanurate (NaDCC) on Angiotensin-Converting Enzyme 2 (ACE 2) Receptor in Accordance with the Present Disclosure The Angiotensin-converting enzyme 2, or ACE2 "receptor" is the protein that provides the entry point for the coronavirus to hook into and infect a wide range of human cells. ACE2 has been also proved to be the receptor for the human respiratory coronavirus NL63, the SARS-coronavirus (SARS-CoV) and the novel coronavirus 2019-nCoV/SARS-CoV-2. The ACE2/Spike inhibition assay allows screening of the potential inhibitors or candidates that can inhibit the interactions between the two targets namely inhibitor and the receptor which results in inhibition of entry of the virus. Drugs targeting the interaction between the Spike protein of SARS-CoV-2 and ACE2 may offer some protection against the viral infection.

NaDCC at various concentrations keeping the peptide DX600 as a positive control using the ACE2 assay kit (BPS #79923) that comes in a convenient 96-well format, with purified ACE2, its substrate, and ACE2 buffer for 96 reactions were tested in the assay. The exopeptidase activity of the ACE2 was measured by the appearance of the fluorescence from the hydrolysis of the florigenic substrate.

Figure 4:
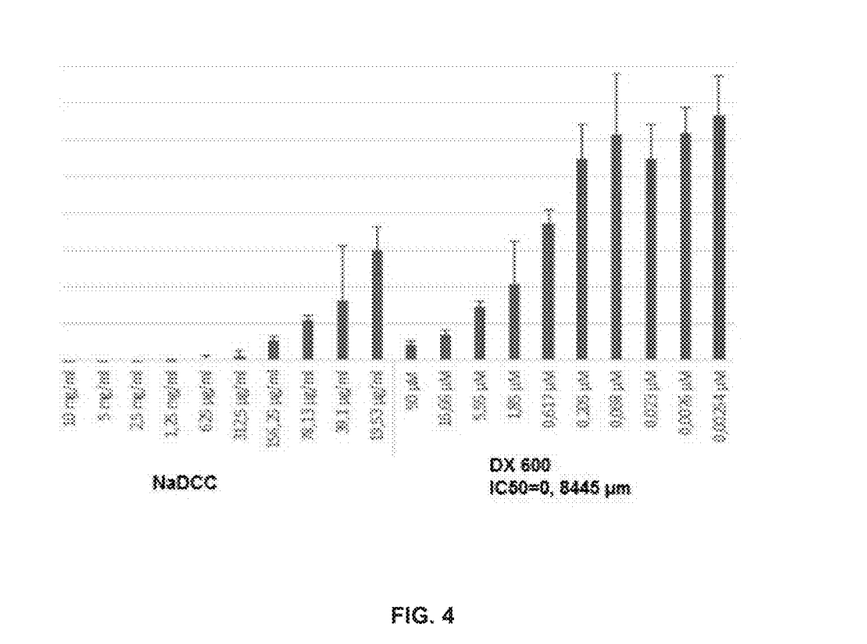
FIG. 4 illustrates an efficacy of NaDCC towards the inhibition of ACE2 receptor.
Figure 5A:
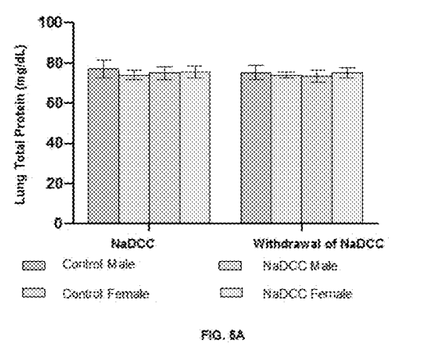
FIG. 5A illustrates effect of NaDCC dry powder inhaler on Lung Total Protein (mg/dL) level.
Figure 5B:
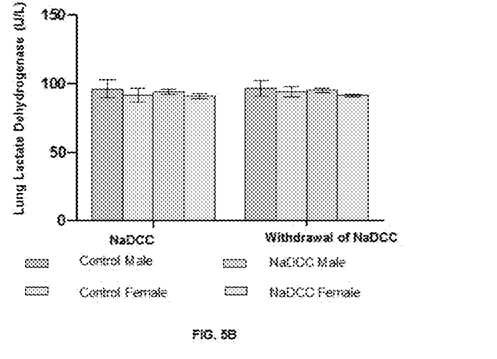
FIG. 5B illustrates effect of NaDCC dry powder inhaler on Lactate Dehydrogenase activity (U/L) level.
Figure 5C:
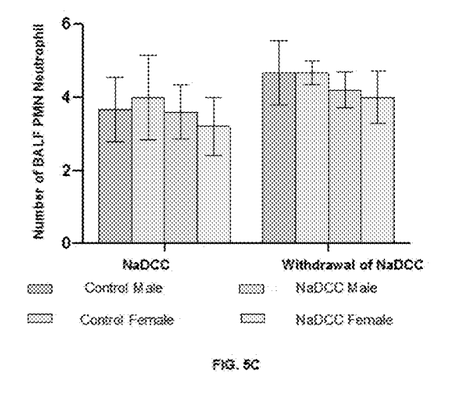
FIG. 5C illustrates effect of NaDCC dry powder inhaler on BALF PMN Neutrophil count.
Figure 5D:
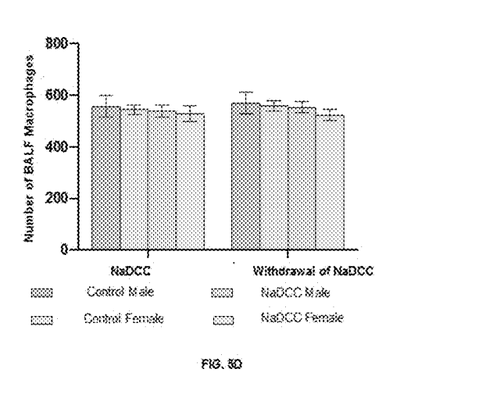
FIG. 5D illustrates effect of NaDCC dry powder inhaler on BALF Macrophages count.
Figure 5E:
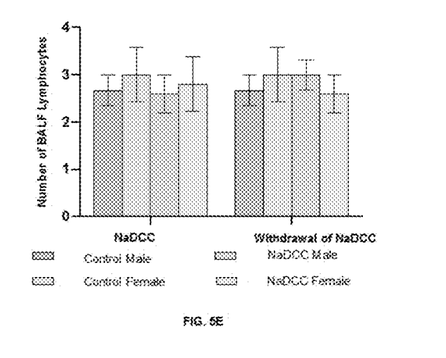
FIG. 5E illustrates effect of NaDCC dry powder inhaler on BALF Lymphocytes count.
Figure 5F:
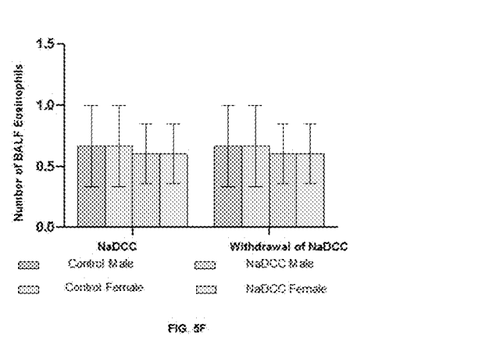
FIG. 5F illustrates effect of NaDCC dry powder inhaler on BALF Eosinophils count.
Figure 6A:
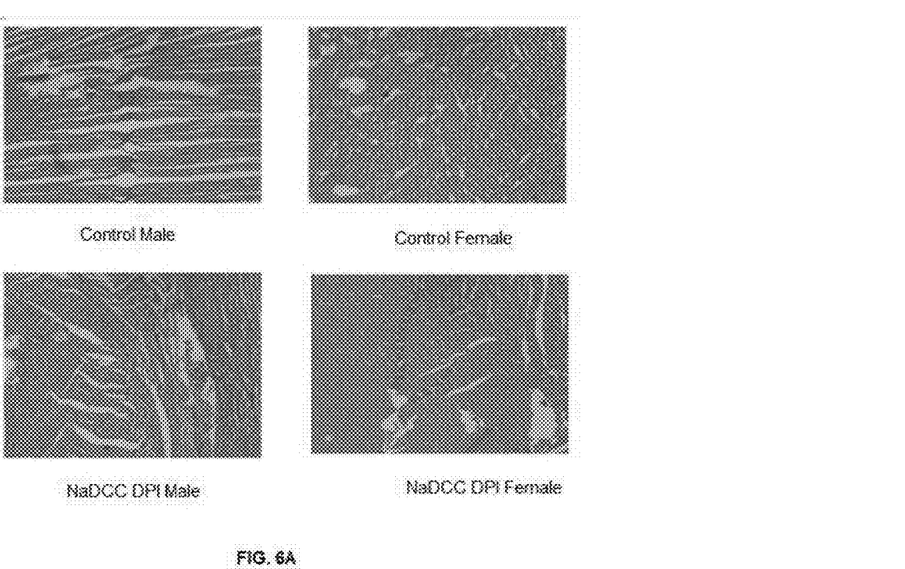
FIG. 6A illustrates effect of NaDCC dry powder inhaler on Histopathology of Lung via transverse section.
Figure 6B:
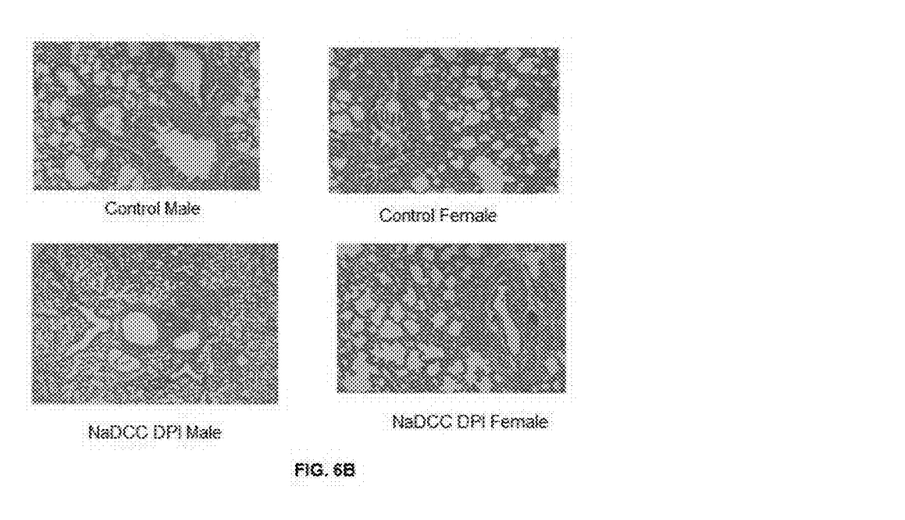
FIG. 6B illustrates effect of NaDCC dry powder inhaler on Histopathology of Lung via cross-section.

FIG. 4 illustrates that the NaDCC effectively inhibits the ACE2 receptor assay at a concentration in the range of 10 mg/ml to 312 μg/ml that amounts to 3.5 to 7 μM. Hence, from the FIG. 4, it is evident that the mode of action of the inhibition of Covid-2 replication by NaDCC is through the inhibition of binding of the spike protein of the virus with the ACE2 receptor present in the host system.

Example 9: Toxicological Studies of NaDCC Dry Powder Inhaler (DPI)

Objectives:
1. To study the effect of NaDCC dry powder inhaler on lungs and Bronchioalveolar lavage fluid.
2. To study the effect of withdrawal after administration of NaDCC dry powder inhaler on lungs and Bronchioalveolar lavage fluid.

Materials:

Wistar Abino Rats of either sex weighing between 200 to 250 g was procured from Global Bioresearch Solutions Pvt Ltd., Pune.

Methods:

Healthy wistar rats of either sex (200-250 g) were purchased from the CPCSEA registered vendor, Pune. Animals were housed under a controlled environmental condition (25±2° C., 12 h dark-light cycle) with free access to pellet diet (Nutri Vet Life Science, India) and water before experiments. During this adaptation phase, the health status of the rats was supervised daily.

Healthy wistar rats (200-250 g) of either sex were divided into two groups such as control and NaDCC DPI treated groups. Ten rats of each sex were assigned to NaDCC DPI while 6 rats of each sex were assigned to Control group. Each animal was given accurate conditioning session for acclimation to the fabricated inhalation apparatus. The animals were dosed with NaDCC DPI using fabricated nose only inhalational chamber for one day. After 24 h, based on the observation, the animals were dosed with NaDCC DPI for 4 more days. At the end of $5^{th}$ day, 5 rats of each sex were sacrificed and the lungs were isolated. The broncho alveolar lavage fluid (BALF) of the right lung was subjected to assay of LDH, total protein and total and differential WBC count while the left lung was used for histopathology. The drug free period of 3 days was given to the remaining animals. They were sacrificed and the left and right lungs were used for histopathology and biochemical, total and differential WBC counts, respectively. The same procedure was followed for control group of animals, except they were administered with air instead of dry powder inhalation of NaDCC.

Preparation and Administration of Doses:

One capsule of NaDCC dry powder inhaler prepared in accordance with the present disclosure containing 7 mg of NaDCC, was administered to one animal using the fabricated nose only inhalational chamber. The fabricated apparatus was used for complete fluidization of formulation allowing the natural nasal inhalation. The fabrication of apparatus was carried out as per the previous reported work. The formulation (capsule content) was placed in the cap and delivery port was covered by cotton wool. The fluidization was carried out for 4 min. The dose administered in animals was 28 mg/kg. Hence, the dose for human is 28×0.78-21.84 mg.

Results:

Effect of NaDCC Dry Powder Inhaler on Lung Total Protein (Mg/dL) Level

The total protein levels in the control groups were found between 74 and 77 mg/dL. Treatment with NaDCC dry powder inhaler in male animals did not cause any significant change of the total protein level in the lung when compared to the control male animals. Treatment with NaDCC dry powder inhaler did not also cause any change of the total protein level in lung in female animals when compared to the control female animals as tabulated in table 10 and FIG. 5A. Hence, upon withdrawal of treatment also, there was no significant change observed in NaDCC dry powder inhaler treated groups when compared to the respective control groups of animals.

Effect of NaDCC Dry Powder Inhaler on Lactate Dehydrogenase Activity (U/L) Level The lactate dehydrogenase level in the control groups were found between 91 and 96 U/L. Treatment with NaDCC dry powder inhaler in male animals did not cause any significant change in lactate dehydrogenase activity when compared to control male animals. Treatment with NaDCC did not also cause any change in lactate dehydrogenase activity in female animals when compared to the control female animals as tabulated in table 10 and FIG. 5B. Hence, upon withdrawal of treatment also, there was no significant change observed in NaDCC dry powder inhaler treated groups when compared to the respective control groups of animals.

Effect of NaDCC Dry Powder Inhaler on BALF PMN Neutrophil Count

The BALF PMN Neutrophil in the control groups were found between 3 and 4. Treatment with NaDCC dry powder inhaler in male animals did not cause any significant change in BALF PMN neutrophils count when compared to control male animals. Treatment with NaDCC dry powder inhaler did not also cause any change in BALF PMN neutrophils count in female animals when compared to control female animals as tabulated in table 10 and FIG. 5C. Hence, upon withdrawal of treatment also, there was no significant change observed in NaDCC dry powder inhaler treated groups when compared to the respective control groups of animals.

Effect of NaDCC Dry Powder Inhaler on BALF Macrophages Count

The BALF Macrophages in the control groups were found between 528 and 556.

Treatment with NaDCC dry powder inhaler in male animals did not cause any significant change in BALF macrophages count when compared to the control male animals. Treatment with NaDCC dry powder inhaler did not also cause any change in BALF macrophages count in female animals when compared to the control female animals as tabulated in table 10 and FIG. 5D. Hence, upon withdrawal of treatment also, there was no significant change observed in NaDCC dry powder inhaler treated groups when compared to the respective control groups of animals.

Effect of NaDCC Dry Powder Inhaler on BALF Lymphocytes Count

The BALF Lymphocytes in the control groups were found between 2 and 3. Treatment with NaDCC dry powder inhaler in male animals did not cause any significant change in BALF lymphocytes count when compared to control male animals. Treatment with NaDCC did not also cause any change in BALF lymphocytes count in female animals when compared to the control female animals as tabulated in table 10 and FIG. 5E. Hence, upon withdrawal of treatment also, there was no significant change observed in NaDCC dry powder inhaler treated groups when compared to the respective control groups of animals.

Effect of NaDCC Dry Powder Inhaler on BALF Eosinophils Count

The BALF Eosinophils in the control groups were found to be between 0 and 1. Treatment with NaDCC dry powder inhaler in male animals did not cause any significant change in BALF eosinophils count when compared to the control male animals. Treatment with NaDCC dry powder inhaler did not also cause any change in BALF eosinophils count in female animals when compared to the control female animals as tabulated in table 10 and FIG. 5F. Hence, upon withdrawal of treatment also, there was no significant change observed in NaDCC dry powder inhaler treated groups when compared to the respective control groups of animals.

Effect of NaDCC Dry Powder Inhaler on Lung Histopathology

The treatment with NaDCC did not alter the lung architecture and alveoli. This was evident by the transverse section of FIG. 6A and cross sections of FIG. 6B of the male NaDCC dry powder inhaler treated animals and female NaDCC dry powder inhaler treated animals as compared to the respective control animals.

TABLE 10

Effect of NaDCC DPI on Lung and Bronchioalveolar Lavage Fluid Parameters

| Parameters | Parameter After | Control (n = 3) Male | Control (n = 3) Female | NaDCC DPI (n = 5) Male | NaDCC DPI (n = 5) Female |
|---|---|---|---|---|---|
| Total Proteins (mg/dL) | Treatment | 77.00 ± 4.51 | 74.00 ± 2.31 | 75.00 ± 3.11 | 75.60 ± 3.04 |
| | Withdrawal | 75.33 ± 3.53 | 74.00 ± 1.53 | 73.40 ± 2.77 | 75.20 ± 2.52 |
| LDH activity (U/L) | Treatment | 96.33 ± 6.64 | 91.67 ± 4.98 | 94.00 ± 2.03 | 91.00 ± 1.95 |
| | Withdrawal | 96.67 ± 5.49 | 94.33 ± 3.84 | 95.20 ± 1.69 | 91.40 ± 0.93 |
| Number of PMN Neutrophils | Treatment | 3.67 ± 0.88 | 4.00 ± 1.16 | 3.60 ± 0.75 | 3.20 ± 0.80 |
| | Withdrawal | 4.67 ± 0.88 | 4.67 ± 0.33 | 4.20 ± 0.49 | 4.00 ± 0.71 |
| Number of Macrophages | Treatment | 556.30 ± 41.07 | 544.00 ± 19.01 | 540.20 ± 23.12 | 528.00 ± 29.87 |
| | Withdrawal | 570.00 ± 41.68 | 559.00 ± 21.13 | 553.40 ± 20.62 | 522.80 ± 22.11 |
| Number of Lymphocytes | Treatment | 2.67 ± 0.33 | 3.00 ± 0.58 | 2.60 ± 0.40 | 2.80 ± 0.58 |
| | Withdrawal | 2.67 ± 0.33 | 3.00 ± 0.58 | 3.00 ± 0.32 | 2.60 ± 0.40 |
| Number of Eosinophils | Treatment | 0.67 ± 0.33 | 0.67 ± 0.33 | 0.60 ± 0.24 | 0.60 ± 0.24 |
| | Withdrawal | 0.67 ± 0.33 | 0.67 ± 0.33 | 0.60 ± 0.24 | 0.60 ± 0.24 |

Inference:

From table 10 it is evident that the administration of dry powder inhaler of NaDCC for 5 days did not cause any change in the male or female animals in the total proteins, lactate dehydrogenase activity, bronchioalveolar lavage fluid-neutrophils, macrophages, lymphocytes or eosinophils as compared to these parameters in control male and control female animals.

NaDCC dry powder inhalation did not change the total protein level, lactate dehydrogenase level in lung tissues which confirm that there is no tissue damage in lung due to administration. There were no changes in neutrophils, macrophages, lymphocytes or eosinophils confirming the lack of inflammatory changes.

Based on the above findings, it was concluded that NaDCC dry powder inhaler did not have toxicity in acute inhalational toxicity test conducted for 5 days. Therefore, the human equivalent dose of NaDCC dry powder inhaler 21.84 mg did not cause any toxicity upon inhalation and is safe to be administered to human.

Technical Advancements

The present disclosure described herein above has several technical advantages including, but not limited to, the realization of, NaDCC is:

- effective against COVID-19 virus, biologically compatible, stable, efficient, economic, non-cytotoxic, and non-allergic;
- is used as a disinfectants for many purposes including wound cleansing, hospital use, water disinfection for human consumption and swimming pool disinfection;
- is used as a teat dip or spray prior to or after milking topically;
- less toxic in terms of teratogenicity and embryotoxicity.

Throughout this specification the word "comprise", or variations such as "comprises" or "comprising, will be understood to imply the inclusion of a stated element, integer or step," or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A pharmaceutical formulation comprising:
    a micronized Sodium 3,5-dichloro-2,4,6-trioxo-1,3,5-triazinan-1-ide (NaDCC) having a particle size in the range of 3 µm to 7 µm;
    a first lactose having a particle size in the range of 15 µm to 120 µm;
    a second lactose having a particle size in the range of 1 µm to 70 µm; and
    at least one excipient;
    wherein the weight ratio of the first lactose to the second lactose is in the range of 4:1 to 10:1;
    wherein said first lactose and second lactose are adsorbed on said micronized Sodium 3,5-dichloro-2,4,6-trioxo-1,3,5-triazinan-1-ide (NaDCC); and
    wherein said pharmaceutical formulation is in the form of an inhalable dry powder.

2. The pharmaceutical formulation as claimed in claim 1, wherein said micronized Sodium 3,5-dichloro-2,4,6-trioxo-1,3,5-triazinan-1-ide is present in an amount in the range of 25 wt % to 65 wt % with respect to the total mass of the formulation.

3. The pharmaceutical formulation as claimed in claim 1, wherein said first lactose is present in an amount in the range of 25 wt % to 65 wt % with respect to the total mass of the formulation.

4. The pharmaceutical formulation as claimed in claim 1, wherein said second lactose is present in an amount in the range of 2 wt % to 15 wt % with respect to the total mass of the formulation.

5. The pharmaceutical formulation as claimed in claim 1, wherein said excipient is at least one selected from the group consisting of glacial acetic acid, cyanuric acid, citric acid, magnesium stearate, hydrophilic colloidal silica and L-Leucine.

6. The pharmaceutical formulation as claimed in claim 1, wherein the median mass aerodynamic diameter of said particles of inhalable dry powder is in the range of 2 µm to 5 µm.

7. The pharmaceutical formulation as claimed in claim 1, wherein the mean particle size (d10) of said first lactose is in the range of 19 µm to 43 µm.

8. The pharmaceutical formulation as claimed in claim 1, wherein the mean particle size (d50) of said first lactose is in the range of 53 µm to 66 µm.

9. The pharmaceutical formulation as claimed in claim 1, wherein the mean particle size (d90) of said first lactose is in the range of 75 µm to 106 µm.

10. The pharmaceutical formulation as claimed in claim 1, wherein the mean particle size (d10) of said second lactose is in the range of 1.4 µm to 3.3 µm.

11. The pharmaceutical formulation as claimed in claim 1, wherein the mean particle size (d50) of said second lactose is in the range of 10.9 µm to 24.9 µm.

12. The pharmaceutical formulation as claimed in claim 1, wherein the mean particle size (d90) of said second lactose is in the range of 32.6 µm to 60.4 µm.

13. The pharmaceutical formulation as claimed in claim 1, wherein said formulation has an antibacterial activity, wound healing activity and antifungal activity.

14. The pharmaceutical formulation as claimed in claim 1, wherein said formulation is used in the treatment and/or prevention of SARS COVID-19 infection, enveloped viruses, EBOLA virus, HIV, HBV, HCV, influenza virus, and MERS.

15. The pharmaceutical formulation as claimed in claim 1, wherein said formulation further comprise at least one anti-viral drug.

16. The pharmaceutical formulation as claimed in claim 15, wherein said anti-viral drug is selected from dexamethasone, Ivermectin, Favipiravir, Ribavirin, Lopinavir, Ritonavir, Remdesivir, Umifenovir, Chloroquine, Hydroxychloroquine, Cyclosporin A, Interferons, and Tocilizumab.

17. The pharmaceutical formulation as claimed in claim 1, wherein said formulation is in a dosage form selected from solution, nasal spray, and hydrogel.

* * * * *